United States Patent
Yan

(10) Patent No.: US 8,993,539 B2
(45) Date of Patent: Mar. 31, 2015

(54) DIETARY FIBER SUPPLEMENTS FOR APPETITE SUPPRESSION

(71) Applicant: Guang Yan, Pocatello, ID (US)

(72) Inventor: Guang Yan, Pocatello, ID (US)

( * ) Notice: Subject to any disclaimer, the term of this patent is extended or adjusted under 35 U.S.C. 154(b) by 0 days.

(21) Appl. No.: 14/033,496

(22) Filed: Sep. 22, 2013

(65) Prior Publication Data

US 2014/0087056 A1    Mar. 27, 2014

Related U.S. Application Data

(60) Provisional application No. 61/704,495, filed on Sep. 23, 2012.

(51) Int. Cl.
| | |
|---|---|
| *A01N 43/04* | (2006.01) |
| *A61K 31/715* | (2006.01) |
| *A23L 1/308* | (2006.01) |
| *A23L 1/0532* | (2006.01) |
| *A61K 31/722* | (2006.01) |
| *A61K 9/00* | (2006.01) |
| *A61K 31/731* | (2006.01) |
| *A61K 31/732* | (2006.01) |
| *A61K 31/734* | (2006.01) |
| *A23L 1/0524* | (2006.01) |
| *A23L 1/056* | (2006.01) |

(52) U.S. Cl.
CPC ............. *A23L 1/3084* (2013.01); *A23L 1/308* (2013.01); *A23L 1/0532* (2013.01); *A61K 31/722* (2013.01); *A61K 9/0095* (2013.01); *A61K 31/731* (2013.01); *A61K 31/732* (2013.01); *A61K 31/734* (2013.01); *A23L 1/0524* (2013.01); *A23L 1/056* (2013.01); *A23V 2200/332* (2013.01); *A23V 2002/00* (2013.01)
USPC ................... 514/54; 514/23; 514/25; 514/55; 514/57

(58) Field of Classification Search
None
See application file for complete search history.

(56) References Cited

U.S. PATENT DOCUMENTS 6,797,290 B2 *   9/2004   Dartey et al. ..................... 426/2

OTHER PUBLICATIONS

Paxman et al. Appetite (2008), vol. 51, pp. 713-719.*
Li et al. Carbohydrate Polymers (2011), vol. 83, pp. 1479-1485.*

* cited by examiner

*Primary Examiner* — Patrick Lewis

(57) ABSTRACT

The present invention provides a composition of dietary fiber supplements for satiety enhancement and appetite suppression in treatment of overweight, obesity, or eating disorders. The composition of the dietary fiber supplements consist of at least one cationic polymer and at least one anionic polymer. The cationic polymers and the anionic polymers in the composition can be dissolved or dispersed in an aqueous solution. When the pH of the aqueous solution is lowered, such as the solution is ingested into the stomach with a gastric pH environment or the aqueous solution is added with some acidifying agents, the aqueous solution will turn into a gel. The formation of a gel from the aqueous solution after it being ingested into the stomach before a meal would provide a satiety enhancement and appetite suppression effect.

7 Claims, No Drawings

DIETARY FIBER SUPPLEMENTS FOR APPETITE SUPPRESSION

CROSS-REFERENCE TO RELATED APPLICATIONS

The present application claims the benefit of U.S. Provisional Application Ser. No. 61/704,495 filed on Sep. 23, 2012, which is hereby incorporated by reference in its entirety.

FIELD OF THE INVENTION

The present invention is in the field of dietary fiber supplements. More particularly, the present invention is in the field of using dietary fiber supplements for satiety enhancement and appetite suppression in treatment of overweight, obesity, or eating disorders.

BACKGROUND OF THE INVENTION

Dieting has been attempted by a lot of people in weight controlling and weight loss. One dieting approach is to increase the consumption of dietary fibers. It has been shown that there is an inverse relationship between the dietary fiber consumption and weight gain (JAMA. 1999 Oct. 27; 282(16): 1539-46.). A lot of dietary fiber supplements are available including alginate, chitosan, pectin, etc.

Alginate is a dietary fiber supplement from seaweeds. Alginate is an anionic polysaccharide with carboxyl groups with pKa from 1.5 to 3.5. Alginate is available in alginic acid and its salt forms including sodium alginate, potassium alginate, calcium alginate, etc. Alginate solution can form gel in the gastric pH or in the presence of calcium or other multivalent ions.

Chitosan is a dietary fiber supplement from shrimp shell. Chitosan is a cationic polysaccharide with amine groups with pKa around 6.5. Chitosan can dissolve in acidic solution. Chitosan oligosaccharide is a type of chitosan with low molecular weight, usually with molecular weight less than 5000. Especially, if the chitosan oligosaccharide has a molecular weight less than 2000, then the chitosan oligosaccharide can dissolve in pure water or even in basic aqueous solutions. In addition, modifications can be made to the chitosan molecule to improve its solubility in water. For example, glycol chitosan is the addition of ethylene glycol group to the chitosan; even with high molecular weight, glycol chitosan can dissolves in pure water and also in basic solutions.

U.S. Pat. No. 2,935,447 (1960) disclosed that taking alginate solution alone or taking alginate solution in combination with some insoluble calcium salts can be used as an appetite depressant. U.S. patent No. 2010/0009932 A1 disclosed that alginate in combination with pectin can form gel in gastric pH for enhancing satiety. U.S. patent No. 2007/0087038 A1 disclosed that addition of a slow releasing acidifying agent into the mixture of alginate with an insoluble calcium salt can promote the gel formation which is less dependent on the gastric pH.

A 12-week clinical study (Am J Clin Nutr doi: 10.3945/ajcn.111.025312) showed that using alginate solution in combination with calcium salt as a preload before meal was more effective to cause weight loss than a placebo preload in obesity patients. The clinical study observed significant side effects such as abdominal pain and distention in the alginate testing group. This could be due to that calcium salts and alginate polymers form gel structure under gastric condition in the stomach, but the formed gel structure is not reversible under an intestinal pH (6.8 to 7.5) and would maintain the gel structure after the gel moving into the intestine, thus cause the abdominal pain and distention. In addition, the using of calcium salts as the gelling ions, especially if the alginate preload being administered three times a day, the amount of calcium intake could exceed the daily upper limit for the calcium suggested from the Office of Dietary Supplement from the National Institute of Health.

The present invention provides a composition of dietary fiber supplements whose aqueous solution can form a gel structure in an acidic condition and the formed gel structure can be reversed back to a solution state in an intestinal pH condition.

SUMMARY OF THE INVENTION

The present invention provides a composition of dietary fiber supplements for satiety enhancement and appetite suppression in treatment of overweight, obesity, or eating disorders. The composition of the dietary fiber supplements consist of at least one cationic polymer and at least one anionic polymer. The cationic polymers and the anionic polymers in the composition can be dissolved or dispersed in an aqueous solution under a neutral to basic condition. When the pH of the aqueous solution is lowered, such as the solution is ingested into the stomach with a gastric pH environment, or the aqueous solution is added with some acidifying agents, the aqueous solution will turn into a gel. The formation of a gel from the aqueous solution after it being ingested into the stomach before a meal would provide a satiety enhancement and appetite suppression effect. The using of cationic polymers in this invention instead of some multivalent metal ions (i.e., calcium ions), to form a gel with the anionic polymers is new. Unlike the gel formed from the anionic polymers with multivalent metal ions, the gel formed from the cationic polymers with anionic polymers is reversible when the solution pH rises to a neutral or basic condition.

DETAILED DESCRIPTION OF THE INVENTION

The present invention provides a composition of dietary fiber supplements for satiety enhancement and appetite suppression in treatment of overweight, obesity, or eating disorders. The composition of dietary fiber supplements consist of at least one polymer which is anionic polymer at pH above 5 and at least one polymer which is cationic polymer at pH below 6. The composition of the dietary fiber supplements with at least one anionic polymer and at least one cationic polymer can be distributed to consumers as a solution formulation, or distributed to consumers as a solid mixture and then the solid mixture can be dispersed into an aqueous solution before ingestion. Then the aqueous solution of the composition of the dietary fiber supplements can form a gel in an acid environment, such as in the stomach after the solution is ingested. A gel mass could be formed in the stomach after the ingestion of the solution. The gel mass could take significant portion of the volume in the stomach. This would make the subjects who have ingested the solution formulation of the dietary fiber supplements or the aqueous dispersion of the solid mixture before their meal, feel less hungry, and thus could lead to less food consumption during the meal. The formed gel mass would gradually move into the intestine through the gastric empting process. With higher pH in the intestine, the cationic polymers would turn into neutral polymers or less positively charged polymers. This could reduce their charge interactions with the anionic polymers, and thus the gel structure would be weakened, or even turned into liquid state.

The anionic polymers in the composition of the dietary fiber supplements discussed above include but not limited to alginic acid or its salts, pectin or its salts, polyacrylic acid or its salts, carbopol polymers, carrageenans, sodium carboxymethyl cellulose.

The cationic polymer in the composition the dietary fiber supplements discussed above include but not limited to chitosan, chitosan oligosaccharides, glycol chitosan, glycol chitosan oligosaccharide, and other modified chitosan derivatives that can be dissolved in aqueous solution at pH above 7.

In addition, one or more acidifying agents can be added into the solution of the composition of the polymers, or the mixture of the composition of the polymers to facilitate the gelling process.

The acidifying agents are the weak organic acids or can be converted to organic acid in aqueous solution. The acidifying agents include but not limited to citric acid, tartaric acid, ascorbic acid, fumaric acid, glucono-delta-lactone.

In addition, a small amount of basic compounds can be added into the solution of the composition of the cationic polymers and anionic polymers to ensure a basic condition for the solution to prevent the gel formation before the solution being ingested into the stomach. A small amount of basic compounds can also be added into the solid mixture of the composition of the cationic polymers and anionic polymers to ensure that after the solid mixture being dispersed into an aqueous solution, the aqueous solution is under basic condition for some period of time (usually from 1 to 10 minute) before ingested into the stomach. The basic compounds include but not limited to sodium bicarbonate, sodium carbonate, potassium bicarbonate, potassium carbonate.

Alginate is an anionic polymer commonly used as a dietary fiber supplement. Sodium alginate is used as an anionic polymer in the examples of the present invention. The sodium alginate used in examples of this invention has a viscosity of less than 500 cp in its 1% aqueous solution. The relatively low viscosity is more suitable for oral ingestion due to easily pouring of the aqueous solution.

Chitosan is a cationic polymer commonly used as a dietary fiber supplement. Low molecular weight chitosan, or chitosan oligosaccharide, when its molecular weight is lower than 3000, more preferably is lower than 2000, even more preferably is lower than 1500, can dissolve in water or even in aqueous solution under a basic condition, such as the pH 7.4. The chitosan oligosaccharide with a molecular weight less than 1500 is used as a cationic polymer in the following examples of the present invention.

Example 1

An aqueous solution contains 1% of the sodium alginate and 0.5% of the chitosan oligosaccharide was prepared. Some sodium bicarbonate (0.1%) was added into the solution to ensure the solution pH higher than 7.4. The final solution had a viscosity less than 500 cp. 200 ml of the final solution was added into 50 ml of 0.08M HCl solution. The HCl solution mimicked the gastric acid condition. The solution with the sodium alginate and chitosan oligosaccharide gelled to form a semisolid mass in 20 min. The viscosity of the semisolid mass exceeded 50,000 cps with a Brookfield viscometer.

Example 2

An aqueous solution contains 1% of the sodium alginate and 0.5% of the chitosan oligosaccharide was prepared. Some sodium bicarbonate (0.1%) was added into the solution to ensure the solution pH is higher than 7.0. The final solution had a viscosity less than 500 cp. In 200 ml of the final solution, 0.6 g of glucono-delta-lactone (GLD) was added and dispersed into the solution. The solution was pourable in the first 2 minutes after the addition of GLD. After 20 min, the solution turned into a semisolid gel. The viscosity of the semisolid gel was too high to be measured.

Example 3

1 part of the sodium alginate, 0.5 part of the chitosan oligosaccharide, 0.1 part of sodium bicarbonate, and 8.4 part of sucrose was mixed together, then the solid mixture was ground with a coffee grinder, and passed through 40 mess sieve. 20 gram of such ground solid mixture was dispersed in 200 ml of water, and was shake vigorously for 2 min. An aqueous dispersion was formed, and the aqueous dispersion was similar to the solution in example 1 with a viscosity less than 500 cp. The aqueous dispersion was added into 50 ml of 0.08M HCl solution. The HCl solution mimics the gastric acid condition. The aqueous dispersion of the alginate and chitosan oligosaccharide mixture gelled into a semisolid mass in 20 min. The viscosity of the semisolid mass exceeded 50,000 cps with a Brookfield viscometer.

Example 4

1 part of sodium alginate, 0.5 part of chitosan oligosaccharide, 0.1 part of sodium bicarbonate, 0.3 part of glucono-delta-lactone, and 8.1 part of sucrose was mixed together, then the mixture was ground with a coffee grinder, and passed through 40 mess sieve. 20 gram of such ground solid mixture was dispersed in 200 ml of water, and was shake vigorously for 2 min. An aqueous dispersion was formed, and the aqueous dispersion was similar to the solution in example 2 with a viscosity less than 500 cp. The aqueous dispersion was pourable in the first 2 minutes after the solid mixture being dispersed in the water. After 20 min, the aqueous dispersion turned into a semisolid gel. The viscosity of the semisolid gel was too high to be measured.

Example 5

Three different aqueous preparations was prepared: Preparation A was an aqueous solution of sodium alginate at a concentration of 0.5%; Preparation B was an aqueous suspension with 0.5% sodium alginate, 0.4% hydroxyapatite $(Ca_{10}(PO_4)_6OH_2)$ powder, and 0.1% sodium bicarbonate in it; and Preparation C was an aqueous solution with 0.5% sodium alginate, 0.5% chitosan oligosaccharide, and adjusted to pH 8.0 with sodium hydroxide. The viscosity of preparation A was 78.5 cp, the viscosity of preparation B was 65.4 cp, and the viscosity of preparation C was 55.0 cp. 10 ml of each of the above preparation was placed into a dialysis tube (Fisher Scientific Inc, 1.9 cm width, MWCO 3000). The dialysis tubes loaded with the preparations were placed in a 0.05M hydrochloride acid solution (200 ml) for 1 hour. After that, the dialysis tube was cut open and the cylindrical shape gel formed in the dialysis tube was collected, and the cylindrical gel was cut into 3 cylindrical disks each with a length around 12 mm. The gel strength of the cylindrical disks was measured with digital force gauge (HF-20) with a flat probe placed on the flat surface of the gel disk. A breaking force was recorded when the gel disk was broken by the applied force. All three preparations formed gel: the gel strength of preparation A was 2.26±0.17 N; the gel strength of preparation B was 6.06±0.37 N; the gel strength from preparation C 1.26±0.15 N.

In a separate setting, the dialysis tubes that loaded with three preparations separately were placed in a 0.05M hydrochloride acid solution for an hour, and then the dialysis tubes were equilibrated in 0.5M tris buffer at pH 8.0 for overnight (16 hours), after that the gel strength from the preparations in the dialysis tune was measured the same way as above, or if the gel disappeared, the solution viscosity in the dialysis tube was measured. The gel structure from preparation A and preparation C disappeared; the gel structure from preparation B (with the calcium ions) maintained. The viscosity of the solution from the preparation A in the dialysis tube was 78.5 cp, same as the original viscosity of the preparation A. The viscosity of the solution from the preparation C in the dialysis tube was also the same as its original solution at 55.0 cp. The gel strength of preparation B was 1.16±0.12 N. These results demonstrated that alginate-calcium gel (preparation B) formed in an acidic condition can not reverse back a solution state in a slight basic environment, while the alginate-chitosan oligosaccharide gel can reverse back to solution state in such condition.

In a separate setting, the three dialysis tube that loaded the three preparations was equilibrated in the 0.5 M acetic acid buffer solution at pH 4.0 for an hour. Preparation A did not form a gel in this condition, and its viscosity was the same as its original solution of 78 cp. This means sodium alginate solution alone cannot form a gel in a stomach with a little high pH environment. Both Preparation B and Preparation C formed gel in the dialysis tubes. The gel strength of preparation B was 9.88±1.25 N. The gel strength of preparation C was 1.18±0.13 N. The gel formed from preparation B maintained its gel form in the 0.5 M tris buffer at pH 8.0, but the gel formed from preparation C was dissolved in the 0.5 M tris buffer at pH 8.0 within an hour.

Example 6

The preparation B (sodium alginate with insoluble calcium salt) and preparation C (sodium alginate with soluble chitosan oligosaccharide), the same as described in Example 5 were prepared. In 10 ml of the preparation B, 0.2 g of an acidifying agent glucono-delta-lactone (GLD) was added and mixed well. In 10 ml of the preparation C, 0.2 g of GLD was also added and mixed well. Both preparation formed gel in 15 min after the addition of GLD. The gel strength from preparation B after the addition of GLD was 7.31 N; and the gel strength from preparation C after the addition of GLD was 3.15 N. Each of the formed gels was put into 20 ml of 0.5M tris buffer at pH 8.0, the gel formed from preparation C was dissolved within 1 hour, but the gel formed from preparation B maintained its gel structure.

In summary of the above examples, the anionic polymer sodium alginate can form a gel structure with the cationic polymer chitosan oligosaccharide in an acid environment or with the addition of an acidifying agent. The formed gel can reverse back to a solution state in a slight basic condition, but the gel formed from sodium alginate and insoluble calcium salt cannot reverse back to a solution state in the slight basic condition.

The advantages of the present invention include, without limitation, (1) a composition of at least one anionic polymer and at least one cationic polymer can be distributed to consumers either as a solution form or as a solid form intend to be dispersed into water before being ingested; (2) a gel can be formed in stomach gastric environment after being ingested; (3) the formed gel can be reversible to fluid liquid in intestinal environments and thus this dietary fiber composition would have the advantage of fewer side effects such as abdominal pain or distension.

While the foregoing written description of the invention enables one of ordinary skill to make and use what is considered presently to be the best mode thereof, those of ordinary skill will understand and appreciate the existence of variations, combinations, and equivalents of the specific embodiment, method, and examples herein. The invention should therefore not be limited by the above described embodiment, method, and examples, but by all embodiments and methods within the scope and spirit of the invention.

I claim:

1. A composition of dietary fiber supplements consists of at least one anionic polymer and at least one cationic polymer for satiety enhancement and appetite suppression.

2. The composition of dietary fiber supplements of claim 1, wherein the anionic polymer is selected from alginic acid or its salts, pectin or its salts, polyacrylic acid or its salts, carbopol polymers, carrageenans, sodium carboxymethyl cellulose.

3. The composition of dietary fiber supplements of claim 1, where the cationic polymer is selected from chitosan, chitosan oligosaccharides, glycol chitosan, glycol chitosan oligosaccharide, and other modified chitosan derivatives that can be dissolved in aqueous solution at pH above 7.

4. The composition of dietary fiber supplements of claim 1, wherein it is distributed to consumers as a liquid for ingestion.

5. The composition of dietary fiber supplements of claim 4, wherein the ingredients in the liquid also include one or more sweeteners, one or more flavors, one or more pH adjusting agents, and one or more acidifying agents.

6. The composition of dietary fiber supplements of claim 1, wherein it is distributed to consumers as a solid to be dispersed in water before being ingested.

7. The composition of dietary fiber supplements of claim 6, wherein the ingredients in the solid also include one or more sweeteners, one or more flavors, one or more pH adjusting agents, and one or more acidifying agents.

* * * * *